(12) United States Patent
Miyatani et al.

(10) Patent No.: US 7,616,302 B2
(45) Date of Patent: Nov. 10, 2009

(54) CONTAINER FOR PROCESSING SECTION SAMPLES, PROCESSING METHOD FOR SECTION SAMPLES, AND PROCESSING APPARATUS FOR SECTION SAMPLES

(75) Inventors: Tatsuya Miyatani, Chiba (JP); Tetsumasa Ito, Chiba (JP)

(73) Assignee: Seiko Instruments, Inc. (JP)

( * ) Notice: Subject to any disclaimer, the term of this patent is extended or adjusted under 35 U.S.C. 154(b) by 132 days.

(21) Appl. No.: 11/795,673

(22) PCT Filed: Jan. 12, 2006

(86) PCT No.: PCT/JP2006/000300

§ 371 (c)(1),
(2), (4) Date: Sep. 25, 2007

(87) PCT Pub. No.: WO2006/082698

PCT Pub. Date: Aug. 10, 2006

(65) Prior Publication Data

US 2008/0088834 A1  Apr. 17, 2008

(30) Foreign Application Priority Data

Feb. 4, 2005  (JP) ............................. 2005-029318

(51) Int. Cl.
*G01N 1/10* (2006.01)
*B01D 53/34* (2006.01)
*C12M 3/00* (2006.01)

(52) U.S. Cl. .................. 356/244; 246/246; 422/100; 422/102; 422/180; 435/287.1; 435/288.4; 204/403.01

(58) Field of Classification Search ............. 356/36–42, 356/244, 246; 422/100, 102, 104, 180, 177; 435/288.4, 287.1, 287.9, 288.7, 294.1; 204/403.01
See application file for complete search history.

(56) References Cited

U.S. PATENT DOCUMENTS

| | | | |
|---|---|---|---|
| 6,561,208 B1 * | 5/2003 | O'Connor et al. | 137/15.18 |
| 6,880,576 B2 * | 4/2005 | Karp et al. | 137/806 |
| 7,244,349 B2 * | 7/2007 | Vogel et al. | 205/777.5 |
| 7,407,630 B2 * | 8/2008 | Reed et al. | 422/102 |
| 7,429,479 B2 * | 9/2008 | Harding | 435/288.4 |
| 2007/0180965 A1 * | 8/2007 | Ito et al. | 83/73 |

FOREIGN PATENT DOCUMENTS

EP  1804047 A2 *  7/2007
JP  04313394 A *  11/1992

* cited by examiner

*Primary Examiner*—Sang Nguyen
(74) *Attorney, Agent, or Firm*—Adams & Wilks

(57) ABSTRACT

The container comprises a cylindrical member 20 which constitutes the side wall member, a bottom member 30 which is in contact with the bottom plane of the cylindrical member 20 and which constitutes the bottom part, and an engaged fixing part 35 for engaging the cylindrical member 20 with the bottom member 30; the cylindrical member 20 and the bottom member 30 sandwiches the carrier tape T from one side T1 of the carrier tape T and from the other side T2 of the carrier tape T, respectively, such that one of the plural thing section samples P1 may be disposed inside the cylindrical member 20. Accordingly, without cutting a sequence of tapes carrying thereon the thin section samples of biomedical tissues, each of the thin section samples of the biomedical tissues can be individually processed with different chemicals depending on the required observation for various types of biomedical tissues.

3 Claims, 11 Drawing Sheets

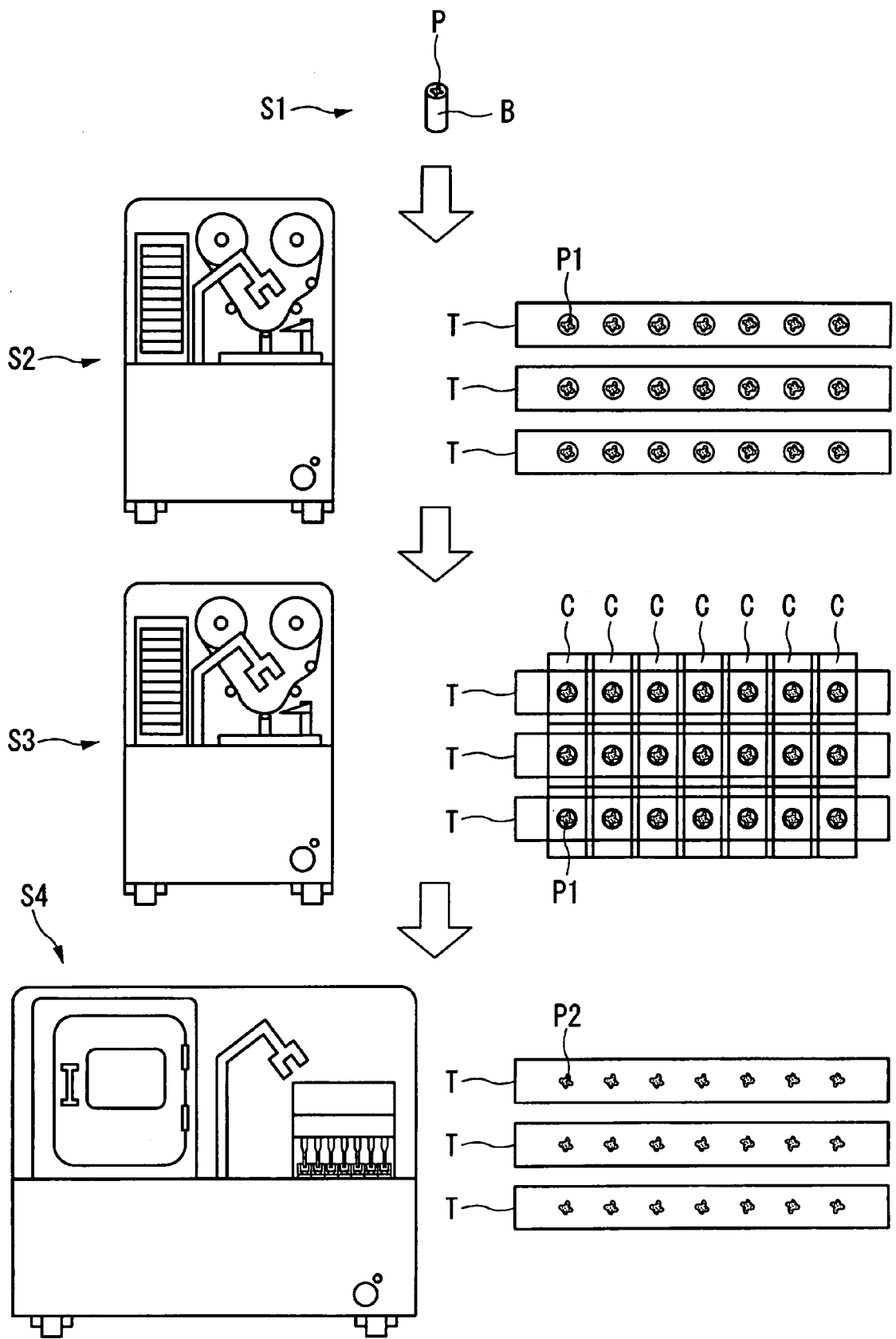

CONTAINER FOR PROCESSING SECTION SAMPLES, PROCESSING METHOD FOR SECTION SAMPLES, AND PROCESSING APPARATUS FOR SECTION SAMPLES

CROSS-REFERENCE TO RELATED APPLICATIONS

This application is a U.S. national stage application of International Application No. PCT/JP200E/300300, filed Jan. 12, 2006, claiming a priority date of Feb. 4, 2005, and published in a non-English language.

TECHNICAL FIELD

The present invention relates to a container for processing section samples, a processing method for section samples, and a processing apparatus for section samples, which are used for processing thin section samples cut out from biomedical samples with the purpose of making observations on the tissues of biomedical samples and the like.

BACKGROUND ART

Conventionally, biomedical tissue samples for use in biomedical tissue observations had to be prepared into samples of thin sections (referred to simply hereinafter as "thin section samples"). Accordingly, a part of the biomedical tissue subject to observations was embedded in a wax and the like to obtain a solid sample, and the biomedical tissue in the solid state was cut out using a microtome and the like to obtain the desired thin section samples. Such biomedical tissue parts embedded in a wax and the like are referred to hereinafter as embedded blocks.

In the case of preparing such thin section samples in large amounts, the edge portions of the aforementioned embedded blocks were adhered to a long carrier tape and the parts in the vicinity of the edge portion were cut out to leave the thin section samples adhered on the carrier tape. Then, the long carrier tape was moved for a predetermined distance, and the edge portion of the embedded block above was adhered to a new site. The vicinity of the edge portion was cut out similarly by repeating the process. By cutting out the thin section samples in this manner, the thin section samples remain held on the carrier tape without flying apart, thus simplifying the repeatedly carried out sequential operations. That is, this process was advantageous in preparing thin section samples in large amount.

On the other hand, as described above, on observing the thin section samples prepared in large amounts, these thin section samples thus obtained had to be treated with chemicals (processing solution). Thus, the thin section samples that have been adhered to the carrier tape were immersed in the chemicals (processing solution) inside a container. Since the thin section samples were adhered sequentially to tapes, it was advantageous to process the thin section samples in the manner above in case they were processed with the same chemical (processing solution), because the thin section samples could be continuously immersed and the process could thereby speeded up.

However, in the modern-day observations of biomedical tissues, it is required to process each of the thin section samples above with different chemicals (for instance, dyeing and the like). On attempting processing the thin section samples using the processing method above, inconveniences were found because the thin section samples were continuously carried adhered to a sequence of tapes. Furthermore, on attempting to cut the sequence of tapes one after another by the part on which the thin section samples were held adhered, inconveniences were found on the positioning for observations.

DISCLOSURE OF THE INVENTION

The present invention has been made in the light of such circumstances, and the objective of the present invention is to provide a container for processing section samples, a processing method for section samples, and a processing apparatus for section samples, which are not only capable of favorably positioning a sequence of tapes carrying thereon the thin section samples of biomedical tissues without cutting the tape in case of observing the thin section samples, but also capable of processing the thin section samples carried on the tape with different types of chemicals depending on the variety of the biomedical tissue. Accordingly, there can be obtained thin section samples processed in such a manner that is capable of responding to the variation of observation on biomedical tissue.

As a means for solving the problems above, the present invention provides a container for processing section samples, a processing method for section samples, and a processing apparatus for section samples.

The container for processing section samples according to the invention relates to a container for processing section samples by immersing, into a processing solution, plural thin section samples that have been adhered on a carrier tape at a predetermined interval, and the container for processing section samples is characterized by that it comprises a side wall member constituting a side wall, a bottom member constituting the bottom part and which is in contact with the bottom plane of the side wall member, and an engaging unit for engaging the side wall member with the bottom member, provided that the side wall member is brought into contact with the bottom member via one side of the carrier tape and the bottom member is brought into contact via the other side of the carrier tape, in such a manner that one of the plural thin section samples may be interposed inside the side wall members, and that the side wall member and the bottom member which are brought into contact via the carrier tape are engaged with the engaging unit.

The container for processing section samples according to the invention comprises a plurality of thin section samples adhered with a predetermined interval on the first side, which is the upper side, of a long carrier tape. The side opposite to the upper side is the lower side, which is denoted as the other side of the carrier tape. The side wall member constituting the wall and the bottom member which is in contact with the bottom plane of the side wall member and which constitutes the bottom part sandwich the carrier tape, i.e., the side wall member is brought into contact from the upper side of the carrier tape and the bottom member from the lower side of the carrier tape, in such a manner that one of the plural thin section samples may be disposed inside the side wall members by forming a container with the side wall member and the bottom member. In this manner, containers each having disposed therein one thin section sample are provided on the carrier tape. This container is provided to each of the plural thin section samples.

Accordingly, in case a processing solution is injected into the container, desired processing can be carried out on each of the thin section samples by individually immersing in the processing solution. Furthermore, because the containers are provided to each of the plural thin section samples, in case different processing solutions are injected to each of the containers, the thin section samples can be individually processed by favorably immersing them into different processing solution to implement the desired processing.

The container for processing section samples according to the invention is characterized by that a plurality of connecting parts which are capable of connecting with each other are provided to either of the side wall member or the bottom member.

In the container for processing section samples according to the invention, a plurality of connecting parts which are capable of connecting with each other are provided to either of the side wall member or the bottom member. Hence, in case there are plural containers, they can be connected with each other. In this manner, the plural containers are mutually connected to form a connected container as if constituting a well plate. Accordingly, for example, in the case of incubating the thin section samples inside an incubator, processing and incubation can be carried out in the same manner as using a well plate. This enables easy handling for observation and other processing. This also contributes for making the container compact.

The container for processing section samples according to the invention is a container for processing section samples by immersing, into a processing solution, plural thin section samples that have been adhered on a carrier tape with a predetermined interval taken among them, and is characterized by that the portions of the carrier tape disposed at a predetermined distance from each other along the longitudinal direction are tightly adhered in such a manner that the carrier tape itself constitutes the side wall and the bottom part, and that one of the thin section samples may be interposed inside the adhered portions.

In the container for processing section samples according to the invention, plural thin section samples are adhered taking a predetermined interval among them on the upper side, which is denoted as the first side, of a long carrier tape. Furthermore, the portion separate from each other by a predetermined distance from one thin section sample along the longitudinal direction of the carrier tape are tightly adhered with each other in such a manner that one thin section sample may be disposed on the upper side (first side) of the carrier tape. In this manner, the carrier tape itself is modified into a container having a side wall and a bottom part. Accordingly, a container having disposed therein one thin section sample is provided on the carrier tape. The plural containers each contain each of the plural thin section samples.

Accordingly, in case a processing solution is injected into the container, desired processing can be carried out on each of the thin section samples by individually immersing them in the processing solution. Furthermore, because the containers are provided to each of the plural thin section samples, in case different processing solutions are injected to each of the containers, the thin section samples can be individually processed by favorably immersing them into different processing solution to implement the desired processing.

The container for processing section samples of the invention is characterized by that a fixing unit is provided for fixing and supporting the tight adhesion between the carrier tape portions.

In the container for processing section samples according to the invention, the tight adhesion established on the carrier tapes free from interstices is fixed and supported by using a fixing unit such as a clip member, to prevent the separation of the tightly adhered portions from occurring. In this manner, as described above, the carrier tape itself is made up into a container, and in case the processing solution is injected into the container, the processing solution can be held in the container almost free from leaking. Accordingly, in the case the processing solution is injected into the container, the thin section samples placed inside the container can be suitably immersed in the processing solution to favorably implement the desired processing.

The processing method for thin sections according to the invention is characterized by that it comprises: an adhesion step for adhering, on one side of an adhesive carrier tape, the edge portion of a sample block comprising a specimen embedded into a embedding material; a cutting out step for cutting out the vicinity of the edge portion of the sample block being adhered on the carrier tape, in such a manner that the thin section sample is left on the carrier tape; a sandwiching step for sandwiching the carrier tape with the side wall member and the bottom part member which constitutes the bottom part and which is in contact with the bottom plane of the side wall member, such that the thin section sample left adhered on the carrier tape may be disposed inside the side wall member constituting the side wall; an engaging step for engaging and supporting each other the side wall member and the bottom member by using an engaging unit; a processing solution injection step for injecting a processing solution for processing the thin section samples into a container made of the side wall member and the bottom member; a processing solution removal step for removing the processing solution from the container after passage of a predetermined time; and a release step for releasing the mutual engaging and supporting of the side wall member and the bottom member that is established by the engaging unit.

In the processing method for section samples according to the invention, a plurality of thin section samples are adhered at a predetermined interval on the first side, which is the upper side, of a long carrier tape. The side opposite to the upper side is the lower side, which is denoted as the other side of the carrier tape. The side wall member constituting the wall and the bottom member which is in contact with the bottom plane of the side wall member and which constitutes the bottom part sandwich the carrier tape; i.e., the side wall member is brought into contact from the upper side of the carrier tape and the bottom member from the lower side of the carrier tape, in such a manner that one of the plural thin section samples may be disposed inside the side wall member by forming a container with the side wall member and the bottom member. In this manner, containers each having disposed therein one thin section sample are provided on the carrier tape. This container is provided to each of the plural thin section samples.

Subsequently, processing solutions for processing the thin section samples are injected, and the thin section samples are immersed in the thus injected processing solution to implement the desired processing. Then, the processing solution is removed from the container, and the side wall member and the bottom member constituting the container are detached from the carrier tape. Accordingly, thin section samples subjected to the desired processing are carried on the carrier tape. Furthermore, because the containers are provided to each of the thin section samples, different processing solutions may be injected individually into each of the containers. Accordingly, thin section samples having processed as desired and differently are carried on the carrier tape.

The processing method for section samples according to the invention is characterized in that it comprises at least two steps of the sandwiching step and the subsequent engaging step that are repeated to provide plural containers on the carrier tape, provided that the containers are each connected to each other with the mutually connectable connecting part provided to each of the containers, and that subsequently the processing solution injection step and the sequent processing solution removal steps are carried out to proceed to the release step.

In the processing method for section samples according to the invention above, in case the thin section samples are processed with the processing solution, the plural containers into which the processing solution is injected are connected with each other with the connecting part provided thereto. In this manner, the plural containers are constituted like a well plate. Accordingly, in the case of processing the thin section samples with the processing solution or incubating inside an incubator, processing or incubation can be favorably carried out.

The processing method for section samples according to the invention is characterized by that it comprises providing plural thin section samples on one side of an adhesive carrier tape by adhering the edge portion of a sample block obtained by embedding a specimen in an embedding material, and for predetermined times, carrying out the process of cutting out the vicinity of the edge portion of the sample block being adhered to the carrier tape, in such a manner that the thin section samples are left on the carrier tape, followed by deforming the carrier tape by tightly adhering portions of the carrier tape disposed at a predetermined distance from each other along the longitudinal direction, in such a manner that the carrier tape itself constitutes the side wall and the bottom part, and that one of the thin section samples may be interposed inside the adhered portions, then injecting into the container a processing solution for processing thin section samples, and removing the processing solution from the container after a predetermined duration of time, and releasing the tightly adhered portions of the carrier tapes.

In the processing method for section samples according to the invention, a plurality of thin section samples are adhered with a predetermined interval on the first side, which is the upper side, of a long carrier tape. Then, for example, the portions of the carrier tapes that are located at a predetermined distance from one thin section sample along the longitudinal direction of the carrier tape are tightly adhered with each other to deform the carrier tape itself into a cylindrical shape to form a cylinder part, such that one thin section sample may be disposed inside the cylinder part, and then tightly adhering one side rim of the carrier tapes free from any interstices, thereby deforming the cylinder part into a container. In this manner, the carrier tape itself is modified into a container having a side wall and a bottom part. The container contains disposed therein one thin section sample.

Subsequently, processing solutions for processing the thin section samples are injected, and the thin section samples are immersed in the thus injected processing solution to implement the desired processing. Then, the processing solution is removed from the container, and the tightly adhered portions, at which the carrier tapes were tightly adhered with each other to constitute the container, are released to recover the original carrier tape for carrying the thin section samples. Accordingly, the carrier tapes carries thereon the thin section samples already subjected to the desired processing. Furthermore, because the containers are provided to each of the thin section samples, different processing solutions may be injected individually into each of the containers. Accordingly, thin section samples having processed as desired and differently are carried on the carrier tape.

The processing method for section samples according to the invention is characterized by that the tightly adhered portions of the carrier tapes are fixed and supported by using a fixing unit after establishing the tight adhesion.

In the processing method for section samples according to the invention, the tight adhesion established on the carrier tapes free from interstices is fixed and supported by using a fixing unit such as a clip member, to prevent the separation of the tightly adhered portions from occurring. In this manner, as described above, the carrier tape itself is made up into a container, and in case the processing solution is injected into the container, the processing solution can be held in the container almost free from leaking. Accordingly, in the case the processing solution is injected into the container, the thin section samples placed inside the container can be suitably immersed in the processing solution to favorably carry out the desired processing.

The processing apparatus for section samples according to the invention is characterized by that it comprises: an adhesion unit which adheres on one side of an adhesive carrier tape, the edge portion of a sample block obtained by embedding a specimen in an embedding material; a cutting out unit which cuts out the vicinity of the edge portion of the sample block adhered to the carrier tape, in such a manner that the thin section samples are left over on the carrier tape; a sandwiching unit which sandwiches the carrier tape with the side wall member and the bottom part member which constitutes the bottom part and which is in contact with the bottom plane of the side wall member, such that the thin section sample left adhered on the carrier tape may be disposed inside the side wall member constituting the side wall; an engaging and supporting unit for engaging and supporting each other the side wall member and the bottom member, by using an engaging unit which mutually engages the side wall member and the bottom member; a processing solution injection unit for injecting a processing solution for processing the thin section samples into a container made of the side wall member and the bottom member; a processing solution removal unit for removing the processing solution from the container after passage of a predetermined time; and a release unit for releasing the mutual engaging and supporting of the side wall member and the bottom member that is established by the engaging unit.

In the processing apparatus for section samples according to the invention, a plurality of thin section samples are adhered taking a predetermined interval on the first side, which is the upper side, of a long carrier tape by using an adhesion unit and a cutting out unit. The side opposite to the upper side is the lower side, which is denoted as the other side of the carrier tape. The side wall member constituting the wall and the bottom member which is in contact with the bottom plane of the side wall member and which constitutes the bottom part sandwich the carrier tape, i.e., the side wall member is brought into contact from the upper side of the carrier tape and the bottom member from the lower side of the carrier tape, in such a manner that one of the plural thin section samples may be disposed inside the side wall member by forming a container with the side wall member and the bottom member. In this manner, containers each having disposed therein one thin section sample are provided on the carrier tape. This container is provided to each of the plural thin section samples.

Then, by using a processing solution injection unit, a processing solution for processing the thin section samples is injected into the container, and the thin section samples are immersed into the processing solution to carry out the desired processing. Subsequently, the processing solution is removed from the container by using a processing solution removal unit, and the side wall member and the bottom member which constitute the container are detached from the carrier tape using a release unit. Thus, thin section samples subjected to the desired processing remain carried on the carrier tape. Furthermore, because the containers are provided to each of the plural thin section samples, in case different processing solutions are injected to each of the containers, the thin section samples can be individually processed by favorably immersing them into different processing solution to implement the desired processing.

The processing apparatus for section samples according to the invention is characterized in that it comprises: an adhesion unit which adheres on one side of an adhesive carrier tape, the edge portion of a sample block obtained by embedding a specimen in an embedding material; a cutting out unit which cuts out the vicinity of the edge portion of the sample block adhered to the carrier tape, in such a manner that the thin section samples are left over on the carrier tape; a carrier tape deformation unit for deforming the carrier tape by tightly adhering portions of the carrier tape disposed at a predetermined distance from each other along the longitudinal direction, in such a manner that the carrier tape itself constitutes the side wall and the bottom part, and that one of the thin section samples may be interposed inside the adhered portions; a processing solution injection unit for injecting a processing solution for processing the thin section samples into a container made of the side wall member and the bottom member; a processing solution removal unit for removing the processing solution from the container after passage of a predetermined time; and a release unit for releasing the mutual engaging and supporting of the side wall member and the bottom member that is established by the engaging unit.

The container for processing section samples according to the invention comprises a plurality of thin section samples adhered taking a predetermined interval on the first side, which is the upper side, of a long carrier tape. Then, by using a deformation unit, for example, the portions of the carrier tapes that are located at a predetermined distance from one thin section sample along the longitudinal direction of the carrier tape are tightly adhered with each other to deform the carrier tape itself into a cylindrical shape to form a cylinder part, such that one thin section sample may be disposed inside the cylinder part, and then tightly adhering one side rim of the carrier tapes free from any interstices, thereby deforming the cylinder part into a container. In this manner, the carrier tape itself is modified into a container having a side wall and a bottom part. The container contains disposed therein one thin section sample.

Subsequently, by using a processing solution injection unit, a processing solution for processing the thin section samples are injected, and the thin section samples are immersed in the thus injected processing solution to implement the desired processing. Then, by using a processing solution removal unit, the processing solution is removed from the container, and the tightly adhered portions, at which the carrier tapes were tightly adhered with each other to constitute the container, are released by using a release unit to recover the original carrier tape for carrying the thin section samples. Accordingly, the carrier tapes carries thereon the thin section samples already subjected to the desired processing. Furthermore, because the containers are provided to each of the thin section samples, different processing solutions may be injected individually into each of the containers. Accordingly, thin section samples having processed as desired and differently are carried on the carrier tape.

BRIEF DESCRIPTION OF THE DRAWINGS

FIG. 1 is a schematically drawn process steps of the method for processing section samples according to the present invention.

BEST MODE FOR CARRYING OUT THE INVENTION

Modes of carrying out the processing method for section samples and the processing apparatus for section samples, together with the processing container for use in the processing method and the processing apparatus, are described below by making reference to figures. Referring to the processing method for section samples according to the invention, as shown in the schematically drawn process steps of FIG. 1, the processing method can be roughly said to comprise a sample block preparation step (S1), a thin section samples preparation step (S2), a container setting step (S3), and a thin section samples processing step (S4). In steps S2 to S3, the figures on the left hand side are the conceptual drawings of the apparatus to be used on the steps, and the figures on the right hand side shows the carrier tape T having adhered thereon the processed thin section sample P1 (before processing) and P2 (after processing). Symbol C represents the container. Thus, various types of specific embodiments for carrying out the processing method are described below.

Embodiment 1

First, a step for preparing a sample block (S1) is described. In the sample block preparation step (S1), a specimen P is embedded in an embedding material to prepare the sample block B. The biological cell for observation is used as the specimen P. Wax, paraffin, or a like material is used as the as the embedding material, and the biological cell as the specimen P is embedded inside the wax or paraffin to obtain the sample block B.

Subsequently, the process proceeds to the thin section samples preparation step (S2), which comprises forming samples of thin sections (referred to hereinafter as "thin section samples") P1 from the thus prepared sample block B, and setting them by adhesion on a carrier tape T. The thin section samples preparation step (S2) includes the adhesion step which comprises adhering the edge portion of the sample block B to one side T1 of the carrier tape T, and a cutting out step comprising cutting out the vicinity of the edge portion of the sample block B thus adhered to the carrier tape T, in such a manner that the thin section sample P1 should be left over on the carrier tape T. Further, the side opposite to the one side T1 of the carrier tape T is denoted as the other side T2 which does not carry thereon the thin section sample P1.

Figure 2A:
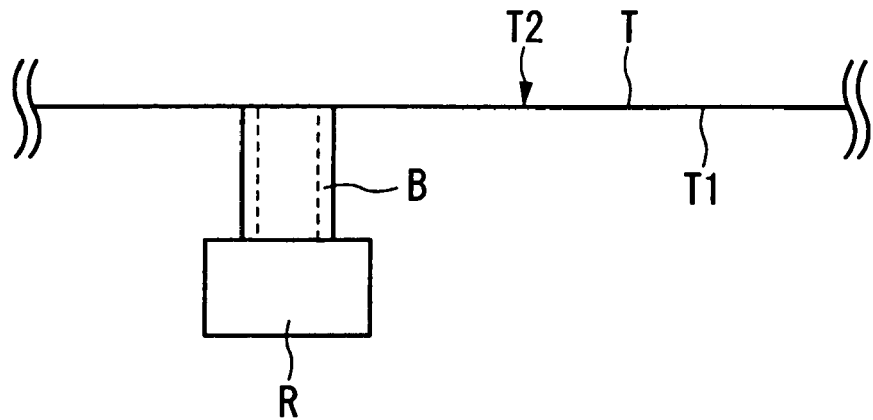
FIG. 2 is a top view showing the adhesion step and the cut-out step.

In the adhesion step as shown in FIG. 2(a), one edge portion of the sample block B is fixed and set on a support table R to support the sample block B with the support table R. Then, the other edge portion of the thus supported sample block B is adhered to the carrier tape T. The carrier tape T is a tape made of a long-sized proper material, and an adhesive is coated on the specified part of the side T1 on which the sample block B is to be adhered. In addition to the support table R, not-shown device for holding the carrier tape T corresponds to the adhesion unit. The adhesive may be coated only to the part onto which the sample block B is adhered, or to the entire surface. Then, the process proceeds to the cutting out step.

Figure 2B:
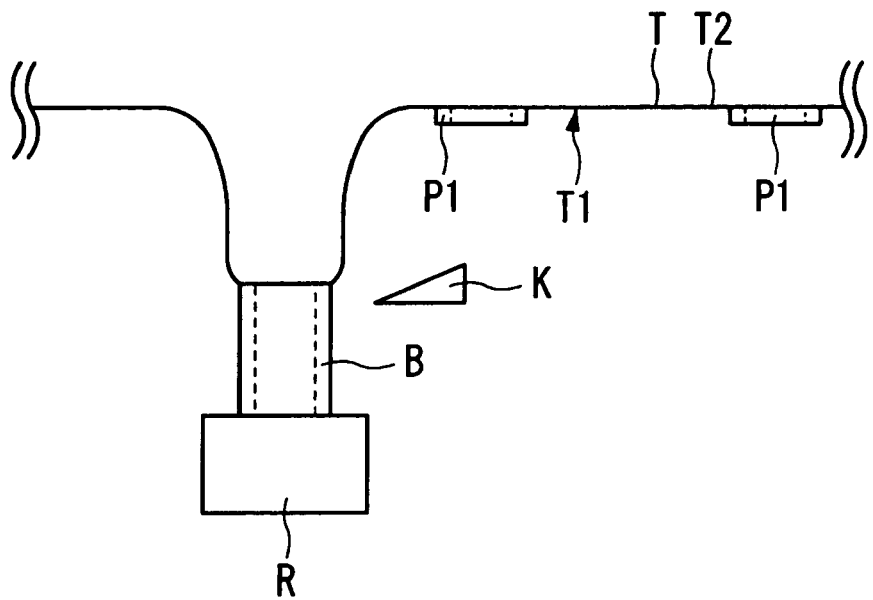

In the cutting out step as shown in FIG. 2(b), the sample block B is cut out with a blade K at the vicinity of the edge portion other than that adhered to the carrier tape T. In this manner, the thin section sample P1 made to a thickness of several tens of micrometers (μm) remain adhered and carried on the carrier tape T. In this instant, the support table R having fixed and adhered thereon the sample block B is pulled apart from the carrier tape T, such that the vicinity of the other edge portion of the sample block B may be easily and suitably cut out. By thus pulling the support table R apart from the carrier tape T, the blade K can be more easily brought into contact with the vicinity of the edge plane of the sample block B, thereby facilitating thinly cutting out the sample block B. The unit equipped with the blade K corresponds to the cutting out unit of the invention.

In the thin section sample preparation step (S2) inclusive of the adhesion step and the cutting out step, the carrier tape T is fed at a predetermined speed and the steps are sequentially repeated such that the thin section samples P1 may be carried on the carrier tape T with a proper interval. Thus, while consecutively confirming, this thin section sample preparation step (S2) is repeated until the thin section samples P1 are accumulated to reach a predetermined amount. After adhering and mounting a predetermined amount of the thin section samples P1 on the carrier tape T in this manner, the process advances to the next container setting step (S3).

Figure 3A:
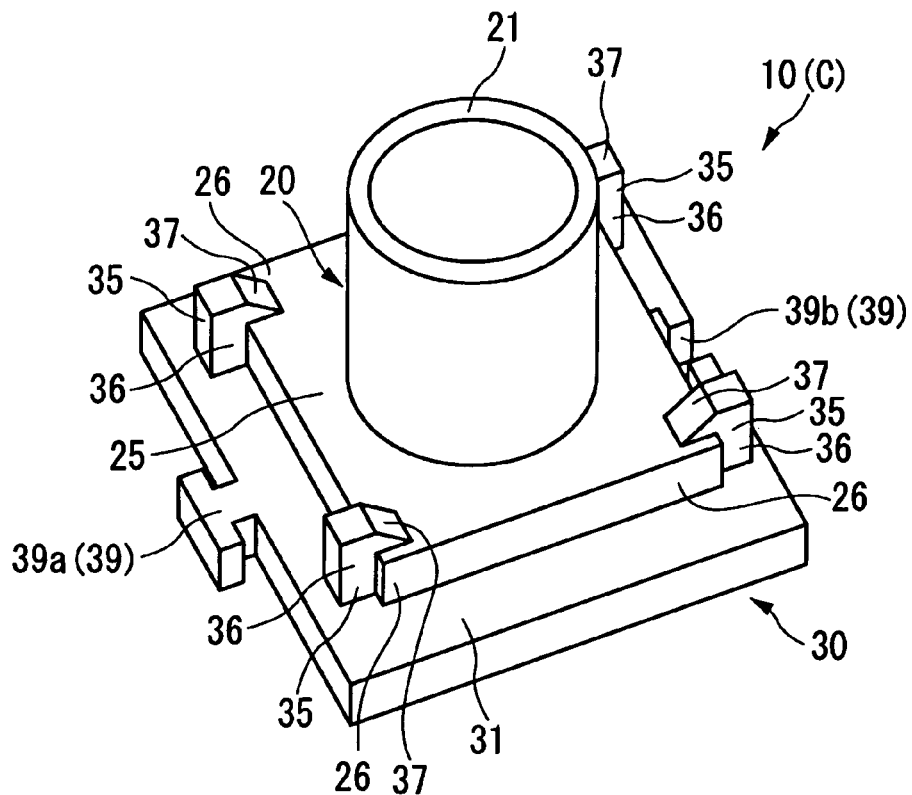
FIG. 3 is an oblique view showing a container member (a container according to the first embodiment of the present invention).
Figure 3B:
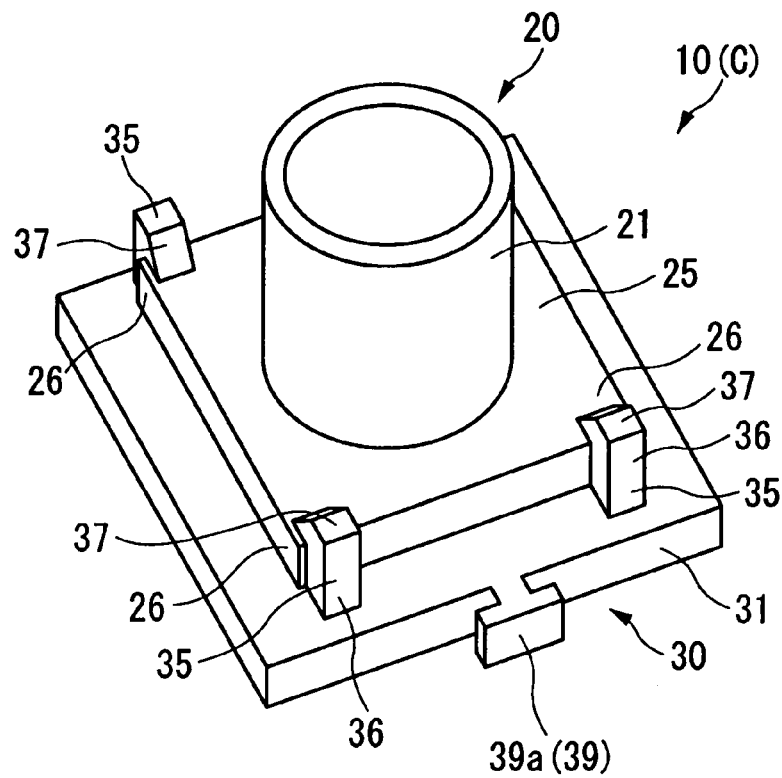

The container setting step (S3) comprises setting a processing container C on the carrier tape T carrying thereon the thin section samples P1. Referring to FIGS. 3(a) and 3(b), in the first embodiment of the invention, this step comprises setting a container member 10 (a container for processing section samples, C) on the carrier tape T. Before describing the container setting step (S3), explanation is given on the container member 10 (a container for processing section samples, C) set in this container setting step (S3).

Figure 6:
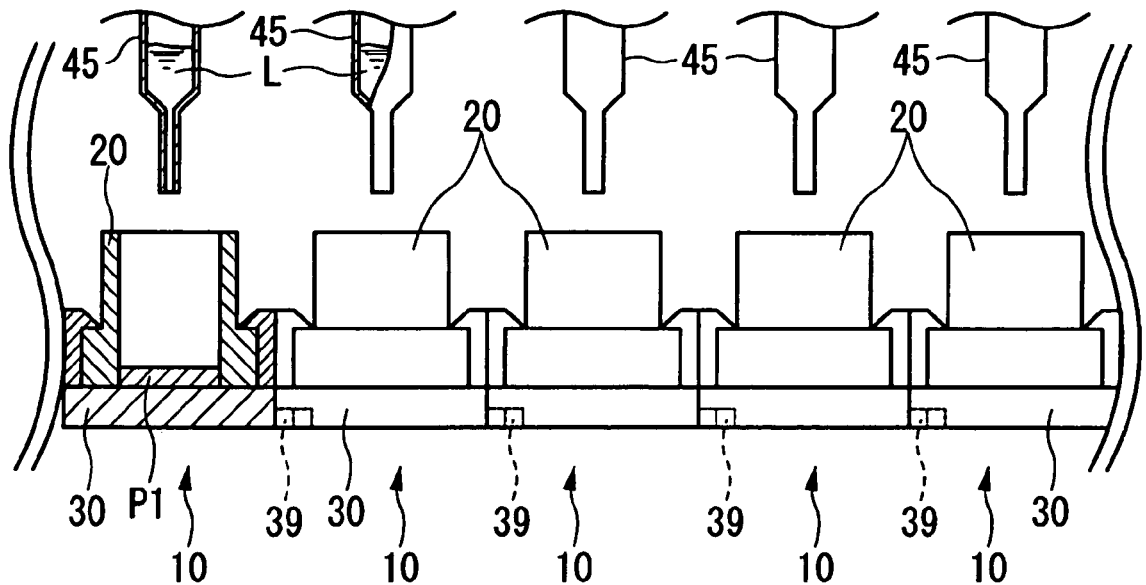
FIG. 6 is a side view showing a step of injecting the processing solution and a step of removing the processing solution.

As described above, the container member 10 corresponds to the container for processing section samples (referring to FIG. 1, a processing container C) of the invention, which is used to immerse the plural thin section samples P1 that are adhered taking a predetermined interval on one side T1 of the carrier tape T in a processing solution L as shown in FIG. 6. The container member 10 comprises a cylindrical member 20 which constitutes the side wall of the processing container C, a bottom member 30 which is brought into contact with the flange part (bottom plane) of the cylindrical member 20 and constitutes the bottom part of the processing container C, and an engaging and fixing part 35 which mutually engages and fixes the bottom member 30 and the cylindrical member 20.

Referring specifically to each of the container members 10, the cylindrical member 20 comprises, as shown in FIGS. 3(a) and 3(b), a cylinder part 21 formed in a cylindrical form and a flange part 25 formed in a flange-like shape at the lower side edge portion of the cylinder part 21 in such a manner that it may be protruded in the direction of the cross section diameter and orthogonal to the axial line of the cylinder part 21. More specifically, the cylinder part 21 is constructed by a cylinder at an inner diameter capable of surrounding the periphery of the thin section samples P1, and at a proper height which makes it possible to, in case a processing solution is injected as described later herein, hold the processing solution L at a proper depth. Furthermore, the flange part 25 is formed in a plate-like shape that is protruded outward from the peripheral end of the lower side edge portion of the cylinder part 21 and in the direction along the diameter, and the outer rim is formed in a square shape. In addition, the length of one side of the outer rim of the flange part 25 is set larger than the width of the carrier tape T, such that it may suitably sandwich the carrier tape T. Accordingly, the flange part 25 favorably covers the carrier tape T. The cylinder part above constitutes the side wall of the container member 10, and the lower plane of the flange part 25 constitutes the bottom plane of the cylindrical member 20.

The cylindrical member 20 should have an inner wall that is brought into contact with the thin section samples P1, which is shaped as such that is capable of surrounding the thin section samples P1 and at a depth capable of holding a predetermined amount of the processing solution L; hence, the shape is not only limited to those that are cylinder-shaped. Any side wall member having a penetrating hole may be used.

Referring to FIGS. 3(a) and 3(b), the bottom member 30 comprises a sheet part 31 formed approximately as a square-shaped flat sheet, and a connecting part 39 that is formed to the periphery of the sheet part 31 in a connectable manner with the connecting part 39 provided to the periphery of another bottom member 30. More specifically, the sheet part 31 is formed larger than the flange part 25 in an approximately square shape, and the upper plane thereof is formed in such a manner that it can be brought into contact with the bottom plane (the lower plane of the flange part 25) of the cylindrical member 20. An O-ring may be interposed by providing it to one of the bottom plane (the lower plane of the flange part 25) of the cylindrical member 20 and the upper plane of the sheet part 31, so that it may bring them into tight contact with each other.

Furthermore, a T-shaped protruded male connector 39a is provided to the side constituting the peripheral part of the sheet part 31, and on the side opposite thereto, a female connector 39b cut in a T-shape to suitably engage with the male connector 39a is provided. The upper side of the sheet part 31 is provided as the upper side of the bottom member 30. Further referring to FIG. 3, only one set of connecting part 39 consisting of the male connector 39a and the female connector 39b is provided to the periphery of the sheet part 31; however, the invention is not only limited thereto, and connecting parts may be provided to the other two planes onto which no connecting part 39 constituting the periphery of the sheet part 31 is set. More specifically, in the sheet part 31, additional connecting parts similar to the pair of male and female connecting parts 39a and 39b may be provided to a plane that is perpendicular to the plane on which the male and female connecting parts 39a and 39b are set. In this case, the container member 10 can be connected two-dimensionally. Further, an engaged fixing part (engaging unit) 35 for engaging the cylindrical member 20 and the bottom member 30 is provided monolithically to the bottom member 30. The engaged fixing part 35 is provided protruded in the direction vertical to the sheet part 31 of the bottom member 30. In the case the bottom plane of the cylindrical member 20 is brought into contact with the upper plane of the bottom member 30, four engaged fixing parts 35 are placed at positions corresponding to the four ends 26 of the outer rim of the flange part 25 provided in square shape. The engaged fixing part 35 comprises a rectangular part 36 formed by the sheet part 31 at a thickness and length corresponding to the flange part 25, and a claw part 37 which is protruded inward and provided integrated with the edge portion of the rectangular part. The claw part 37 is formed with a lower plane that is in parallel with the sheet part 31 and that is located on the side to which the rectangular part 36 is provided, and the upper plane opposed to the lower plane is formed in a tapered form that is slanted to the inward direction.

By thus forming the engaged fixing part 35, in the case the bottom plane of the cylindrical member 20 is brought into contact with the upper plane of the bottom member 30, the flange part 25 can be favorably engaged with the engaged fixing part 35 (engaging unit) 35. In other words, the engaged fixing part 35 (engaging unit) 35 favorably engages the cylindrical member 20 and the bottom member 30. The connecting part 39 is provided to the periphery of the sheet part 31 of the bottom member 30 constituting the container member 10, however, the invention is not only limited to this constitution, and may be constituted as such that it may be provided to the periphery of the cylindrical member 20. Furthermore, the engaged fixing part 35 (engaging unit) 35 is constituted monolithically with the bottom member 30, however, the invention is not only limited thereto, and it may be constituted as a monolithic member with the cylindrical member 20, or may be constituted by a new member separately from the cylindrical member 20 and the bottom member 30.

In the container setting step (S3), the container member (the container C for processing section samples) 10 thus constituted is provided to the carrier tape in the following manner. The container setting step (S3) comprises a sandwiching step for sandwiching the carrier tape T with the cylindrical member 20 and the bottom member 30, an engaging step using the engaged fixing part 35 for mutually engaging the cylindrical member 20 and the bottom member 30, and retaining the engagement, and a connecting step for mutually connecting the connecting parts 39 provided to each of the container members 10.

Figure 5:
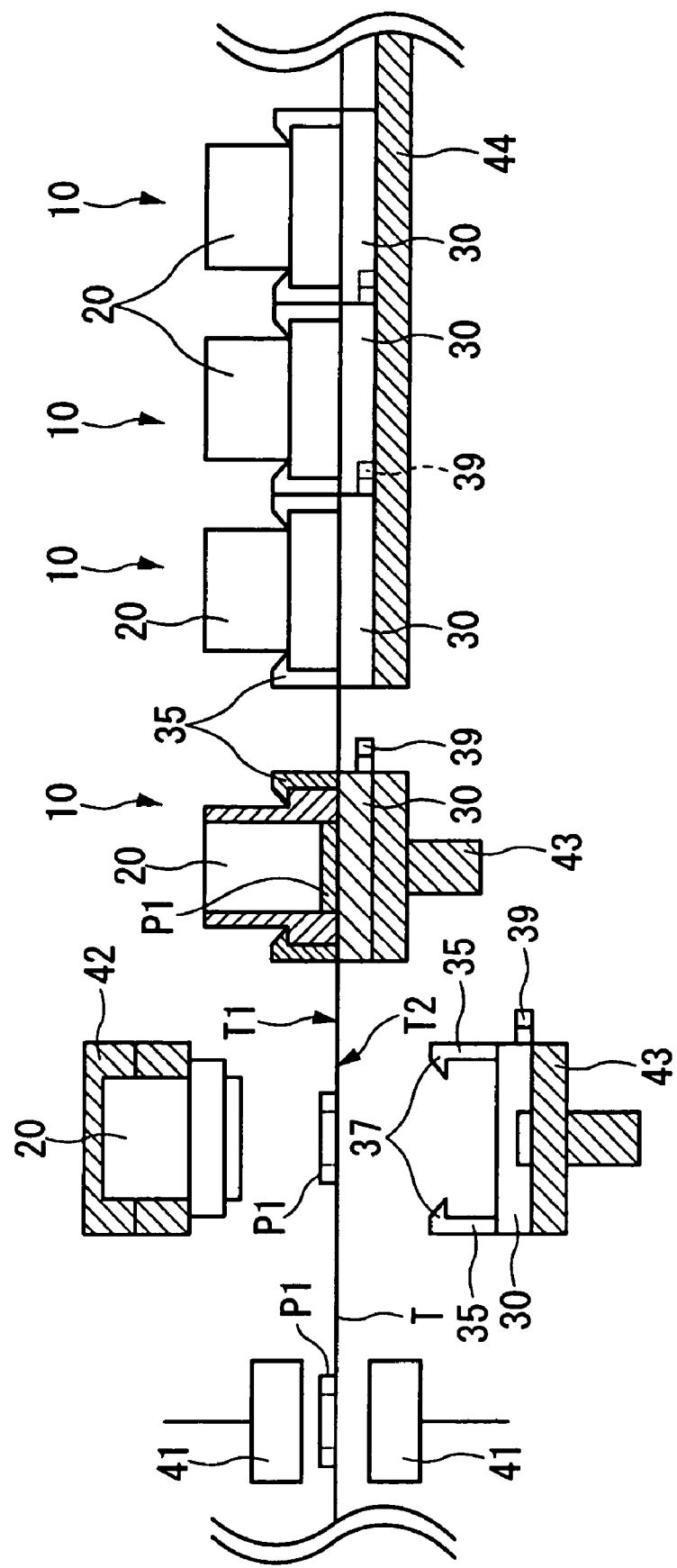
FIG. 5 is a side view showing a step of sandwiching a carrier tape with a cylindrical member and a bottom member.

In the sandwiching step referring to the left hand side of FIG. 5, a position detection sensor 41 provided as a section position detection unit is used to detect at which position the thin section samples P1 are carried on the carrier tape T. The position detection sensor 41 images the carrier tape T with an imaging device equipped with a proper image processing device, and the image is processed with the image processing device to detect at which position the thin section samples P1 are carried on the carrier tape T. As is described further below, by using a cylinder member clamping mechanism (cylinder member clamping unit) 42 and a bottom member clamping mechanism (bottom member clamping unit) 43, the thin section samples P1 can be disposed inside the cylinder part 21 of the cylindrical member 20 in case the carrier tape T is sandwiched with the cylindrical member 20 and the bottom member 30. In this case, the unit equipped with the position detection sensor 41, the cylinder member clamping mechanism 42, and the bottom member clamping mechanism 43 corresponds to the sandwiching unit of the invention. Furthermore, the cylinder member clamping mechanism 42 and the bottom member clamping mechanism 43 correspond to the engaged support unit.

After once detecting the position of the thin section samples P1 carried on the carrier tape T, the carrier tape is sandwiched with the cylindrical member 20 and the bottom member 30 in such a manner that the center axial line of the thus detected thin section samples P1 may become coaxial with the center axial line of the cylinder part 21 of the cylindrical member 20. More specifically, as shown in the center of FIG. 5, the carrier tape T carrying thereon the thin section samples P1 is sandwiched, while allocating the cylindrical member 20 clamped by the cylinder member clamping mechanism 42 on the upper side and the bottom member 30 clamped by the bottom member clamping mechanism 43 on the lower side. Then, the cylinder member clamping mechanism 42 and the bottom member clamping mechanism 43 are operated as such that the cylindrical member 20 and the bottom member 30 approach each other to sandwich the carrier tape T, in such a manner that the center axial line of the thin section samples P1 may become coaxial with the center axial line of the cylinder part 21 of the cylindrical member 20. Subsequently, the process proceeds to the engaging step in which the cylindrical member 20 and the bottom member 30 are engaged to form the container member 10.

In the engaging step referring to the center of FIG. 5, the claw part 37 of the engaged fixing part (engaging unit) 35 provided to the bottom member 30 is extended to the upper side of the flange part 25 to engage the cylindrical member 20 with the bottom member 30. In this manner, the carrier tape T carrying thereon the thin section samples P1 is sandwiched to constitute the container member 10 by mutually engaging the cylindrical member 20 and the bottom member 30. In this instance, the claw part can be smoothly extended to the upper side of the flange part 25 because the upper side of the claw part 37 is tapered. Subsequently, the process proceeds to the connecting step to mutually connect the thus constituted container members 10.

In the connecting step referring to the right hand side of FIG. 5, the plural container members 10 constituted in the sandwiching step and the engaging step above are connected with each other by using the connecting part 39 provided to each of the bottom members 30 as a part of the container members 10. More specifically, the bottom member clamping mechanism 43 clamps the container members 10, and the bottom member clamping mechanisms 43 are brought close to each other in such a manner that the container members 10 approach each other, and the male connecting part 39a is fitted with the female connecting part 39b. Thus, the container member 10 forms an integrated row as if constituting a well plate. After the container members 10 are connected, the part of the member of the bottom member clamping mechanism 43 is detached to provide a container member support table 44.

In this manner, a container member (a container C for processing section samples) 10 is provided on the carrier tape T. This step is then followed by a thin section samples processing step (S4) for processing the thin section samples P1. In this connecting step, the connection of the container members 10 may be carried out properly when necessary, while excluding the container setting step (S3). The thin section samples processing step (S4) is a step for processing the thin section samples, and it comprises a processing solution injection step for injecting the processing solution L for processing the thin section samples P1 into the container members 10, a processing solution removal step comprising removing the processing solution L from the container members 10 after immersing thin section samples P1 in the processing solution L for a predetermined duration of time, and a release step for detaching the container members 10 from the carrier tape T. The release step is carried out by releasing the mutual engaged retention of the engaged fixing part 35 provided as the engaging unit for the cylindrical member 20 and the bottom member 30.

The processing solution injection step referring to FIG. 6 comprises injecting a processing solution L for processing the thin section samples P1 into the well-plate like connected plural container members 10 produced in the container setting step (S3). In the processing solution injection step, a processing solution exchange dropper unit 45 which double functions as a processing solution injection unit and a processing solution removal unit according to the invention injects the processing solution L into the container members 10. The processing solution exchanging dropper unit 45 is constituted in such a manner that plural units may be allocated depending on the interval and the number of the well-plate like connected container members 10, and that the processing solution L may be injected or removed.

After the processing solution L is injected into the container members 10, the thin section samples P1 placed inside the container members 10 are immersed in the processing solution L. Until a predetermined time elapses after the thin section samples P1 are immersed in the processing solution L, so that they can be favorably processed, the thin section samples P1 remain in the immersed state. After the elapse of predetermined time, the step proceeds to the processing solution removal step for removing the processing solution L from the container members 10. The processing solution L may be for instance, chemicals for dyeing the thin section samples P1, but is not limited thereto and any type of chemicals may be used for processing the thin section samples P1. Furthermore, during the thin section samples P1 are immersed in the processing solution L after the processing solution L is injected into the container members 10, it may be constituted in such a manner that the container members 10 inclusive of the thin section samples P1 are placed inside a proper incubator box to carry out proper type of incubation.

The processing solution removal step comprises removing, from the container members 10, the processing solution L that has been injected into the container members 10 in the processing solution injection step. In the processing solution removal step, the processing solution L inside the container members 10 is suctioned out using the processing solution exchange dropper unit 45 which also functions as the processing solution removal unit, to thereby remove the processing solution L from the container members 10. In this manner, the thin section samples P2 processed by the processing solution L remain inside the container members 10 still held by the carrier tape T.

In the processing solution injection step and the processing solution removal step above, the thin section samples P1 may be subjected only once to these steps, or may be subjected repeatedly to these steps depending on the requirement of the observer. For instance, limited number of thin section samples P1 may be dyed red (the processing solution is a red-color dye solution), and then, the some of the rest of the section samples P1 may be dyed blue (the processing solution is a blue-color dye solution). After the thin section samples P1 are processed once or plural times depending on the requirements of the observer in this manner, the process proceeds to a release step for removing the container members 10 from the carrier tape T carrying thereon the thin section samples P2.

The release step is a step for releasing the container members 10 from the carrier tape T. More specifically, it is a step for releasing the mutually engaged retention of the cylindrical member 20 and the bottom member 30 provided by the engaging unit, i.e., the engaged fixing part 35. In the release step, as can be understood from the container members 10 shown in FIG. 3, the cylindrical member 20 is slid over the bottom member 30 by using a not shown sliding mechanism utilized as the release unit in the invention, to thereby remove the cylindrical member 20 from the bottom member 30. In this manner, the container members 10, that is, the cylindrical member 20 and the bottom member 30 which were constituted monolithically by the engaged fixing part 35, are each detached from each other, and the sandwiched carrier tape T is also released. Accordingly, the container members 10 are detached from the carrier tape T. The cylindrical member 20 can be detached from the bottom member 30 by releasing the claw part 37 of the engaged fixing part 35 provided to the bottom member 30 from the flange part 25 of the cylindrical member 20; that is, the container members 10 can also be removed from the carrier tape T.

Figure 4:
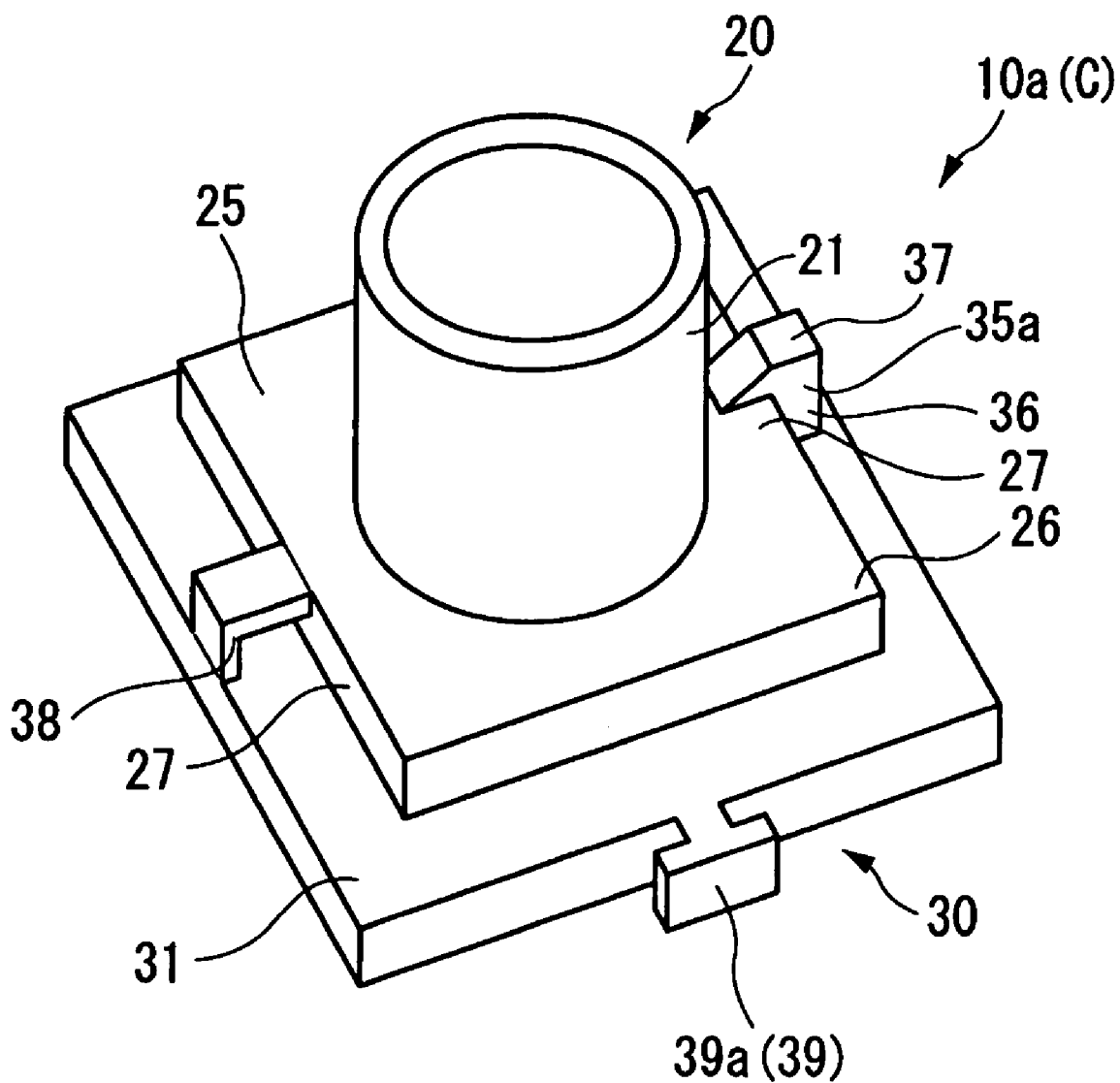
FIG. 4 is an oblique view showing a modified example of the container member (a container according to the first embodiment of the present invention).

The container member (the container C for processing section samples) 10 that has been set in the container setting step (S3) according to the first embodiment of the invention may be constituted as follows. For the parts constituted in the same manner as in the container member 10 above, the same symbols are attached to omit the explanation. That is, as shown in FIG. 4, a second container member 10a provided as a modified example of the container member 10 comprises, similar to the container member 10, a cylindrical member 20 constituting the side wall of the processing container C, a bottom member 30 in contact with the flange part (bottom plane) 25 of the cylindrical member 20 constituting the bottom part of the processing container C. The second container member 10a differs from the container member 10 in the point that an engaged fixing part (engaging unit) 35a is provided to the bottom member 30, and that a connecting part 38 for connecting the cylindrical member 20 with the bottom member 30.

Differing from the four engaged fixing parts 35 of the container member 10, which were provided in correspondence to the four edges 26 in the outer rim of the flange part 25, the engaged fixing part 35a of the second container member 10a is only one and is provided at the center position of the side parts 27 constituting the outer rim of the flange part 25. The engaged fixing part 35a of the second container member 10a is constituted in such a manner that the position in the sheet part 31 and the number differ from those provided to the container member 10 above, but that the other constitutions are similar to the engaged fixing part 35 of the container member 10. That is, the engaged fixing part 35a comprises a rectangular part 36 formed by the sheet part 31 at a thickness and length corresponding to the flange part 25, and a claw part 37 which is protruded inward and provided integrated with the edge portion of the rectangular part. The claw part 37 is formed with a lower plane that is in parallel with the sheet part 31 and that is located on the side to which the rectangular part 36 is provided, and the upper plane opposed to the lower plane is formed in a tapered form that is slanted to the inward direction.

Furthermore, in the second container member 10a, a connecting part 38 which connects the cylindrical member 20 with the bottom member 30 is provided to the side part 27 opposed to the engaged fixing part 35a. The connecting part 38 comprises one end that is connected to the flange part (bottom plane) 25, and the other end that is connected to the upper plane of the sheet part 31. This retains the connection between the cylindrical member 20 and the bottom member 30, and prevents the cylindrical member 20 and the bottom member 30 from falling apart in case the engagement between the engaged fixing part (engaging unit) 35a and the flange part 25 is released. Furthermore, a slit is formed on the connecting part 38 at such a width that flexibility can be imparted to the part. Accordingly, in case the engagement between the engaged fixing part 35a and the flange part 25 is released, the connecting part 38 itself bends favorably to maintain a suitable distance between the bottom plane (lower plane of the flange part 25) of the cylindrical member 20 and the upper plane of the sheet part 31.

As described hereinbefore, by using the processing method for section samples according to the invention, container members 10 each having placed therein one thin section sample P1 are provided on a carrier tape T. The container members 10 are provided to each of the plural thin section samples P1. Accordingly, in case a processing solution L is injected to the container members 10, the thin section samples P1 placed inside the container members 10 can be favorably immersed in the processing solution L to preferably carry out the desired processing. Furthermore, because the container members 10 are provided to each of the plural thin section samples P1, in case each of the container members 10 are injected with processing solutions L differing from each other, the thin section samples P1 can be favorably immersed into different processing solutions L to carry out the desired processing depending on the observation required for each of the various biomedical tissues. In addition, because the carrier tape carrying thereon the sequence of thin section samples P1 need not to be cut, on observing the thin section samples P2, positioning can be similarly facilitated as in the conventional method to make the observation of the thin section samples P1 under a favorable state.

Further, because the plural container members 10 are mutually connected, the container members 10 can be constituted as if constituting a well plate. Accordingly, in case of incubating the thin section samples P1 in an incubator, for instance, processing and incubation can be carried out in the same manner for well plates, thus facilitating the observations and other processing operations.

Embodiment 2

Then, the second embodiment which differs from the first embodiment is described below. In the description below, reference is made to only the steps that are constituted differently from the first embodiment above, and the explanations are omitted for the steps that are constituted similar to those of the first embodiment. More specifically, in the second embodiment, the container setting step (S3) alone is different from the first embodiment. Accordingly, the container setting step (S3) of the second embodiment is described below.

Thus, similar to the first embodiment above, the container setting step (S3) is carried out sequent to the sample block preparation step (S1) and the thin section samples preparation step (S2).

Figure 7:
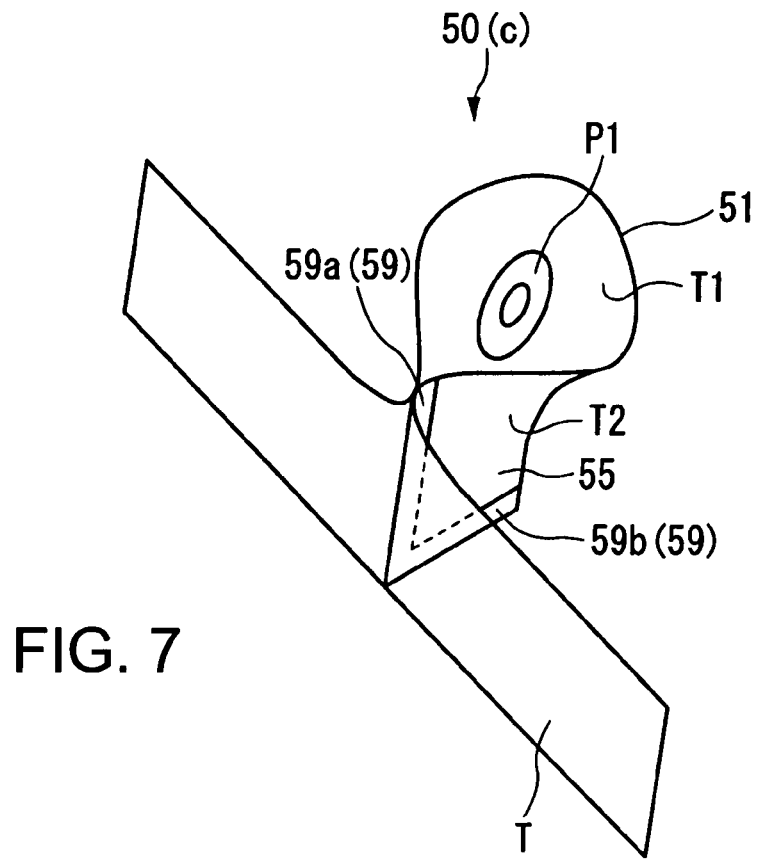
FIG. 7 is an oblique view showing a container part (a container according to the second embodiment of the present invention).

Similar to the first embodiment, the container setting step (S3) of the second embodiment comprises setting a processing container C on the carrier tape T carrying thereon the thin section samples P1; in the second embodiment, the carrier tape T itself is modified into a container-like container unit (container C for processing section samples) 50 as shown in FIG. 7. Before describing the container setting step (S3), explanation is made on the carrier tape-T itself that is modified into a container-like container unit (container C for processing section samples) 50 for use in the container setting step (S3).

Similar to the container members 10, the container unit 50 corresponds to the processing container (processing container C shown in FIG. 1) of the invention, and is used for processing plural thin section samples P1 being adhered at a predetermined interval on one side T1 of the carrier tape T by immersing the samples in a processing solution L. The container unit 50 as shown in FIG. 7 is constituted by deforming the carrier tape T itself, such that the carrier tape T itself constitutes the container unit 50 by providing the side wall part (side wall) 51 and the bottom part 55. Further, one thin section sample P1 among the plural thin section samples P1 is placed and held inside the container unit 50. The symbol 59 (59a and 59b) shows the tightly adhered part at which the carrier tapes T tightly adhere to each other.

That is, the container unit 50 comprises a tightly adhered part 59 (59a) provided by tightly adhering the carrier tape T at the part that is distant from one of the thin section samples P1 by a predetermined distance along the longitudinal direction, and by tightly adhering one side rim (the lower side rim shown in the figure) of the carrier tape T to provide the tightly adhered part 59 (59b). By thus providing a tightly adhered part 59 on the carrier tape T in this manner, the carrier tape T is deformed in such a manner that the side wall part 51 and the bottom part 55 are formed. Thus, by forming the side wall part 51 and the bottom part 55 on the carrier tape T, a container unit 50 formed in a container-like shape and having one thin section sample P1 placed inside is provided on the carrier tape T as a result. The container unit 50 thus obtained is formed in the container setting step (S3) that is described below.

Although the details are given hereinafter, in brief, the container setting step (S3) according to the second embodiment comprises tightly adhering the carrier tape T at the part that is distant from one of the thin section samples P1 by a predetermined distance along the longitudinal direction to deform the carrier tape T into a cylindrical cylinder part 50a in such a manner that one of the thin section samples P1 is placed inside, and by then tightly adhering one side rim of the carrier tape T in such a manner that no interstices may be present, thereby deforming the cylinder part 50a in a container-like shape and forming a container unit 50. In detail, the container setting step (S3) is as follows.

Figure 8A:
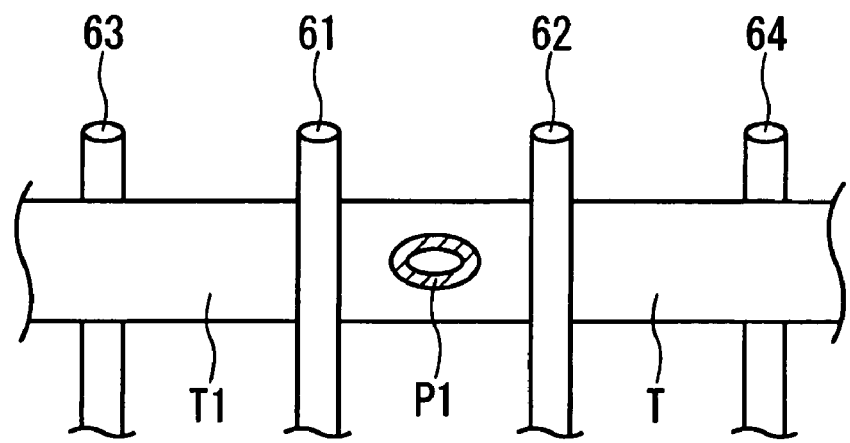
FIG. 8 is an oblique view and a top view showing the step of forming a container unit.
Figure 8B:
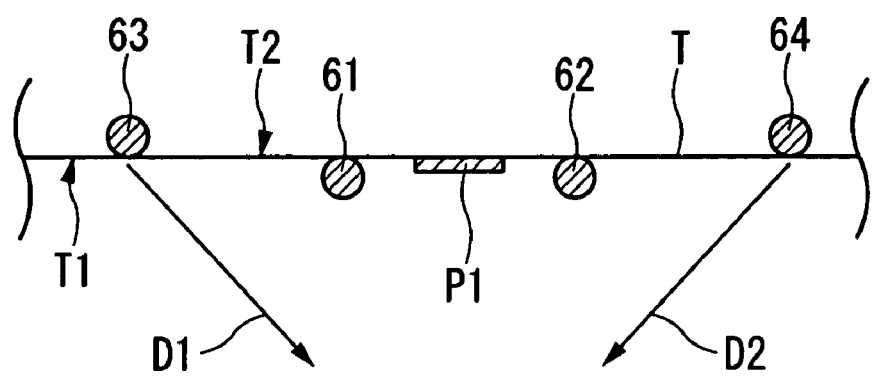
Figure 9A:
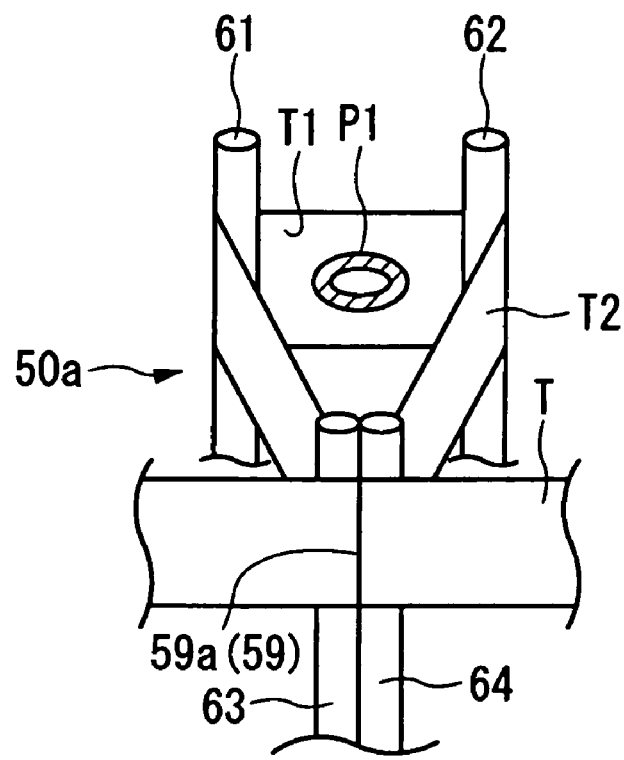
FIG. 9 is an oblique view and a top view showing the step of forming a container unit.
Figure 9B:
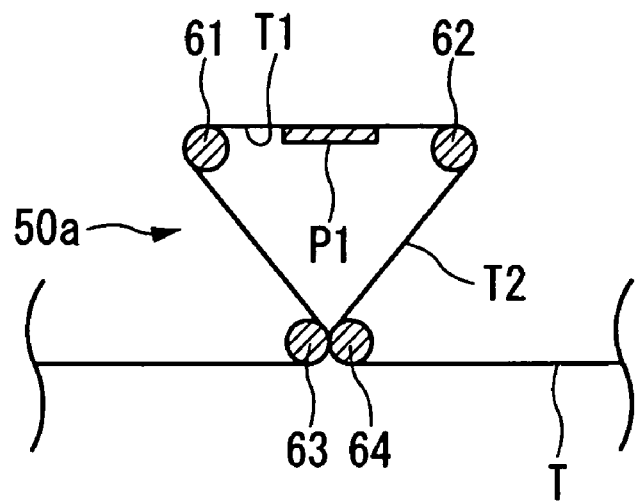
Figure 10A:
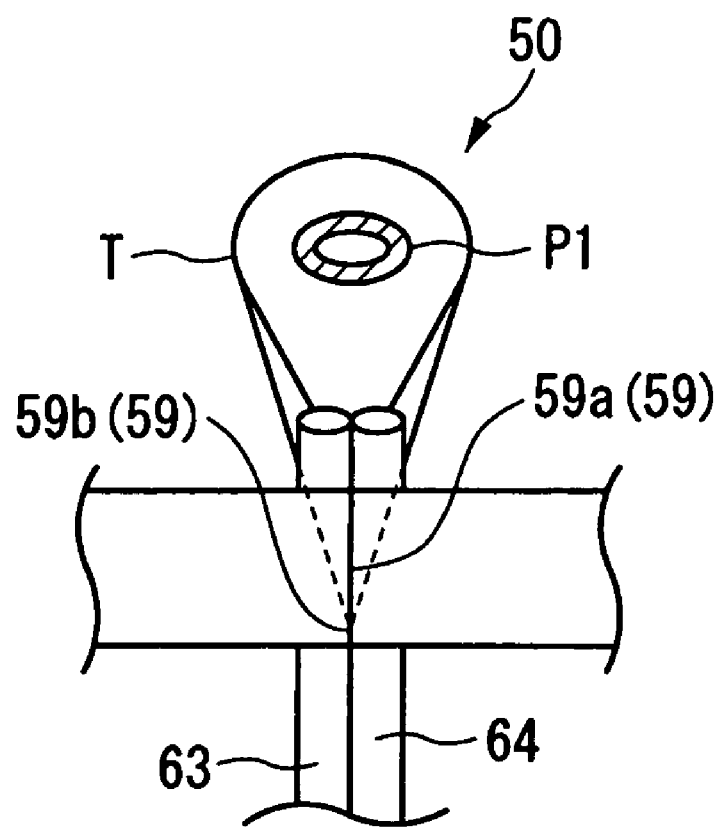
FIG. 10 is an oblique view and a top view showing the step of forming a container unit.
Figure 10B:
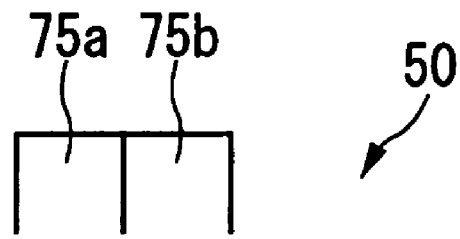

That is, referring to FIGS. 8 to 10, the container setting step (S3) according to the second embodiment comprises deforming the carrier tape T itself by using a tape supporting rod provided as a carrier tape deformation unit of the invention. FIG. 8(a) is an oblique view showing a first tape supporting rod and a second tape supporting rod placed with respect to the carrier tape T; FIG. 8(b) is a top view corresponding to FIG. 8(a); FIG. 9(a) is an oblique view showing the formation of a first tightly adhered part by moving the second tape supporting rod with respect to the first tape supporting rod; FIG. 9(b) is a top view corresponding to FIG. 9(a); FIG. 10(a) is an oblique view showing the formation of a second tightly adhered part; and FIG. 10(b) is a side view showing the container unit to which a clip member is provided for fixing and supporting the first tightly adhered part and the second tightly adhered part.

Firstly, as shown in FIGS. 8(a) and 8(b), the carrier tape T is disposed in such a manner that the sides (one side T1 and the other side T2) are vertically set. In this case, the carrier tape T is placed as such that the side T1 carrying thereon the thin section samples P1 faces the front. Then, two first tape supporting rods 61 and 62 are set in contact with the first side T1 and separated from each other at a predetermined distance but with the thin section sample P1 interposed between them, in such a manner that they are disposed along the width direction but perpendicular to the longitudinal direction of the carrier tape T. Furthermore, two second tape supporting rods 63 and 64 set in contact with the other side T2 opposed to the first side T1 and separated from each other at a predetermined distance longer than those of the first tape support rods 61 and 62 but with the thin section sample P1 and the tape supporting rods 61 and 62 interposed between them, in such a manner that they are disposed along the width direction but perpendicular to the longitudinal direction of the carrier tape T. The apparatus equipped with the first tape supporting rods 61 and 62, as well as the second tape supporting rods 63 and 64 corresponds to the carrier tape deformation unit of the invention.

Then referring to FIG. 8(*b*), the second tape supporting rods 63 and 64 are moved to the side of the first side (in the figure, to the side facing the front) D1 and D2, while keeping the first tape supporting rods 61 and 62 fixed and bringing the second tape supporting rods 63 and 64 closer to each other. In this manner, as shown in FIGS. 9(*a*) and 9(*b*), the first tightly adhered part 59*a* is formed by bringing the second tape supporting rods 63 and 64 closer to each other and tightly adhering the carrier tape T. Thus, the carrier tape T is deformed into a cylindrical cylinder part 50*a* with the thin section sample P1 held therein.

Subsequently, as shown in FIG. 10(*a*), the tape supporting rods 61 and 62 are drawn out from the cylinder part 50*a*, and the first side rim (lower side rim) of the cylinder part 50*a* is tightly adhered free from interstices to form a second tightly adhered part 59*b* (59). In this case, the other side rim (upper side rim) of the cylinder part 50*a* is left open. Thus the cylinder part 50*a* is modified into a container unit 50.

Then, referring to FIG. 10(*b*), a clip member (a fixing unit of the invention) 70 is provided to the container unit 50 thus obtained by the deformation of the carrier tape T, to thereby fix and support the tight adhesion of the first tightly adhered part 59*a* and the second tightly adhered part 59*b* constituting the container unit 50. As seen in the side view in FIG. 11, the clip member is approximately L-shaped, and is made of a metal to which a slit part 71 is provided to make an approximately L-shaped cross section. Furthermore, the clip member 70 comprises an opening 72, so that the slit part 71 may be properly opened. The opening 72 has an insert member 73 inserted and fixed therein.

Figure 11:
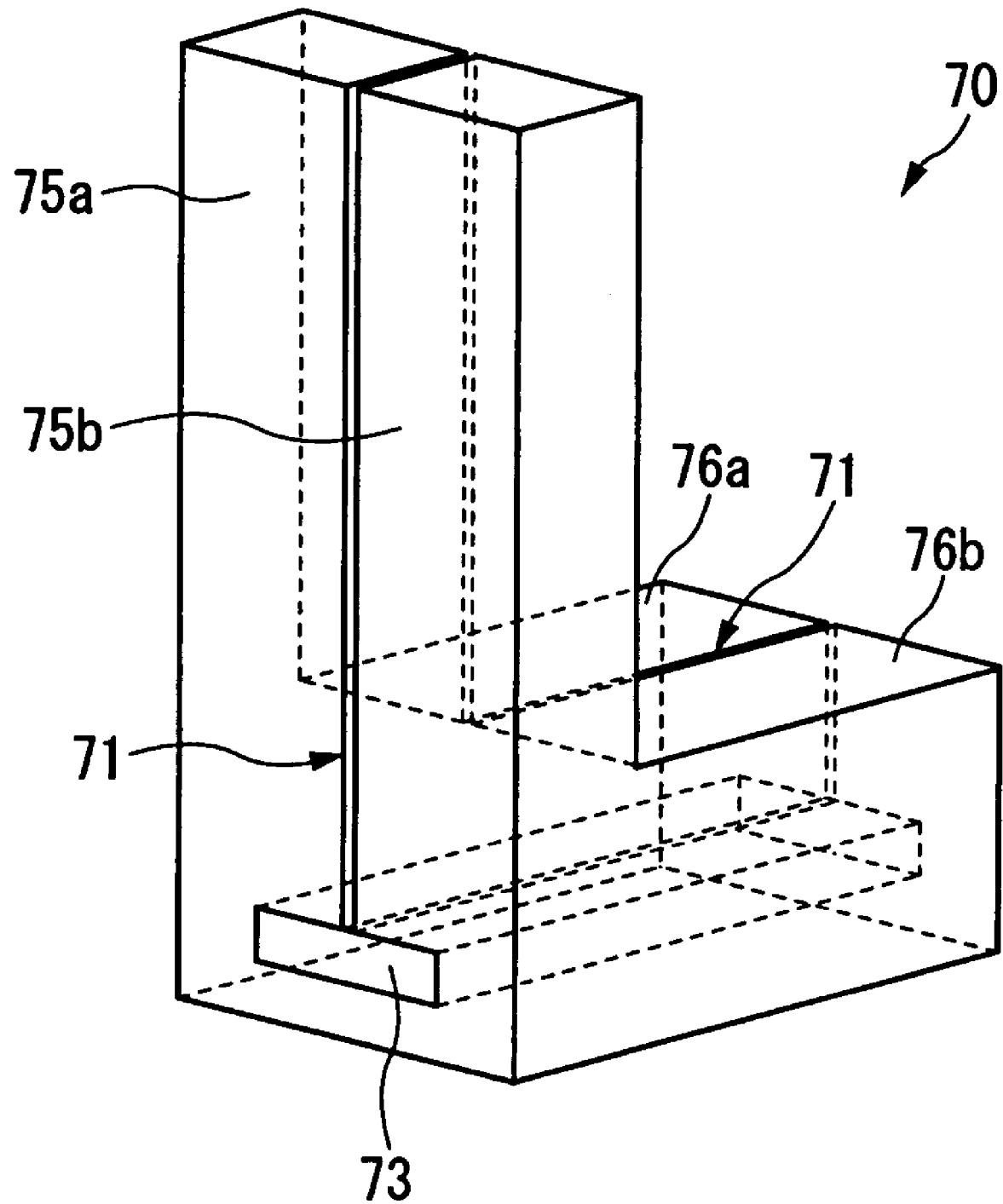
FIG. 11 is an oblique view of a clip member (a fixing unit).

That is, as shown in FIG. 10(*b*) and FIG. 11, the first tightly adhered part 59*a* is clamped and fixed by the first clamping parts 75*a* and 75*b* of the clip member 70, and the second tightly adhered part 59*b* is clamped and fixed by the second clamping parts 76*a* and 76*b* of the clip member 70. In this manner, the container-like constituted container unit 50 is fixed with the clip member 70, and the process proceeds to the subsequent thin section samples processing step (S4) for processing thin section samples P1. In the thin section samples processing step (S4), the thin section samples P1 are processed in the same manner as in the first embodiment.

In the second embodiment also, similar to the first embodiment described above, a container unit 50 which corresponds to the container C for processing section samples is provided on the carrier tape T. Accordingly, the thin section samples P1 are suitably immersed in the processing solution L and favorably processed during the thin section samples processing step (S4) inclusive of the processing solution injection step and the processing solution removal step. In the release step of the second embodiment, the clip member 70 is detached from the container unit 50, and the tight adhesion between the carrier tapes T is released at the first tightly adhered part 59*a* and the second tightly adhered part 59*b*, to thereby recover the original shape of the carrier tapes T. Proper unit can be adopted as the release unit for the carrier tapes T; for instance, appropriate tape supporting rods 61 and 62 may be pushed against the tightly adhered parts 59*a* and 59*b* for separation.

Figure 12A:
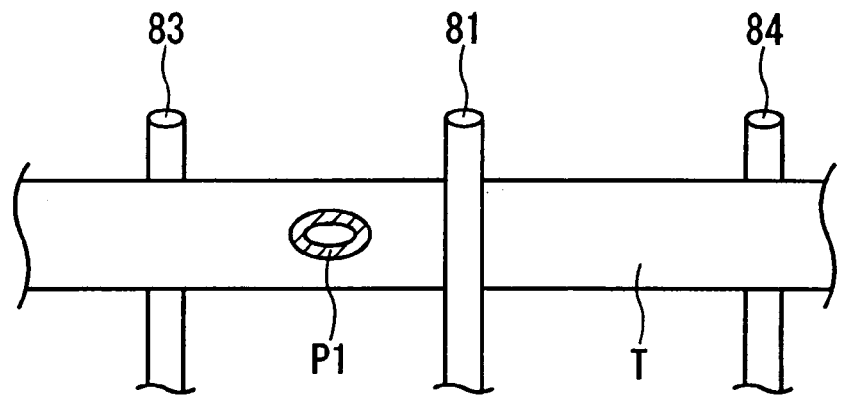
FIG. 12 is an oblique and a top view of a modified example of the step for forming a container unit.
Figure 12B:
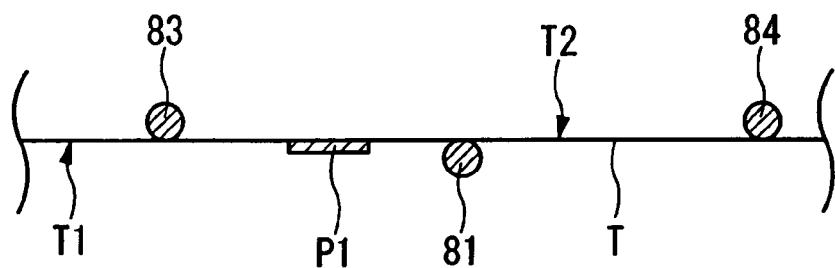
Figure 12C:
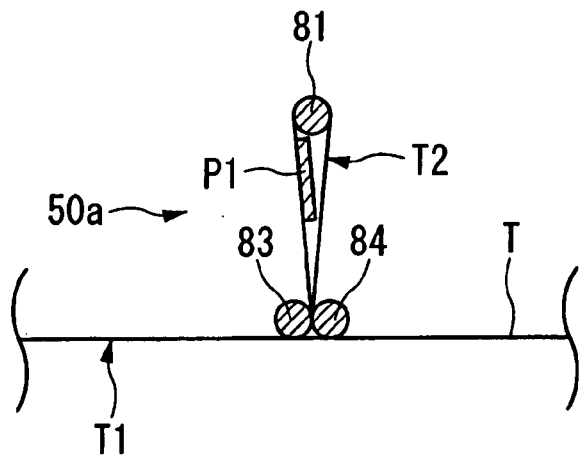

The container setting step (S3) of the second embodiment may otherwise be implemented in the following manner. The modified container setting step (S3) according to second embodiment is described below by making reference to FIG. 12. In the modified example, the container setting step (S3) of the second embodiment is carried out in a similar manner as above, except for the method for forming the first tightly adhered part 59*a*. Accordingly, explanation is made only on the method for forming the first tightly adhered part 59*a*, and the explanations on the subsequent step of forming the second tightly adhered part 59*b* and the like are omitted. FIG. 12(*a*) is an oblique view showing the first tape supporting rod and the second tape supporting rod being placed in relation with the carrier tape T; FIG. 12(*b*) shows the top view of FIG. 12(*a*); and FIG. 12(*c*) is the top view showing the formation of the first tightly adhered part by moving the second tape supporting rod towards the first tape supporting rod.

First referring to FIGS. 12(*a*) and 12(*b*), the carrier tape T is disposed in such a manner that the sides (first side and the other side) are set vertical. In this case, the side T1 of the carrier tape T carrying thereon the thin section samples P1 is disposed to face the front side. Then, one first tape supporting rod 81 is set at a predetermined distance from the thin section sample P1 and in contact with the first side T1, in such a manner that it is disposed along the width direction of the carrier tape T that is perpendicular to the longitudinal direction of the carrier tape T. Furthermore, two second tape supporting rods 83 and 84 are set in contact with the other side T2 opposed to the first side T1 above and separated from each other at a predetermined distance but with the thin section sample P1 and the first tape supporting rod 81 interposed between them, in such a manner that the rods are disposed along the width direction of the carrier tape T that is perpendicular to the longitudinal direction of the carrier tape T.

Subsequently, referring to FIG. 12(*c*), the second tape supporting rods 83 and 84 are moved to the side of the first side (in the figure, to the side facing the front) while keeping the first tape supporting rod 81 fixed, and bringing the second tape supporting rods 83 and 84 closer to each other. In this manner, the first tightly adhered part 59*a* is formed by bringing the second tape supporting rods 83 and 84 closer to each other and tightly attaching to the carrier tape T. Thus, the carrier tape T is deformed into a cylindrical cylinder part 50*a* with the thin section sample P1 held therein. Then, as described in the second embodiment with reference to FIG. 10(*a*), the cylinder part 50*a* is deformed to form a vessel-like container part 50 by tightly attaching the first side rim (lower side rim) of the cylinder part 50*a* free from interstices to form the second tightly adhered part 59*b*.

In case a processing solution L is injected into the container unit 50, the thin section samples P1 placed inside the container unit 50 can be favorably immersed in the processing solution L to carry out the desired processing. Furthermore, since the container unit 50 is provided to each of the plural thin section samples P1, by injecting different processing solution L to each of the container units 50, the thin section samples P1 can be suitably immersed to different processing solutions L to favorably carry out the desired processing per each sample. In addition, since this sequence of carrier tape carrying thereon the thin section samples P1 need not be cut, the positioning can be easily implemented on observing the thin section samples P2 as in the conventional method to make the observation of the thin section samples P1 under a favorable state.

Furthermore, the tight adhesion of the parts that have been tightly adhered by using a fixing unit such as a clip member 70 free from interstices is fixed and retained. In this manner, as described above, the carrier tape T itself is made up into the container unit 50, and in case the processing solution L is injected into the container unit 50, the processing solution L can be held in the container unit 50 almost free from leaking. Accordingly, the thin section samples P1 placed inside the container unit 50 can be suitably immersed in the processing solution L to favorably carry out the desired processing.

As described above, by employing, the processing method for section samples, a carrier tape T carrying thereon the thin section samples P2 having subjected to desired process can be obtained. Furthermore, the thus obtained carrier tape T carrying thereon the thin section samples P2 can be used on a proper observation apparatus to observe the biomedical samples depending on the observer's requirement.

The invention is not only limited to the embodiments above, and proper selections can be made so long as they do not deviate the idea of the invention. For instance, the connecting unit described above in the embodiments were such constituted by a T-shape protruded male connecting part 39a and a female connecting part 39b capable of being fitted to the male connecting part 39a, however, the invention is not only limited to this example, and any constitutions comprising a pair of male and female parts that are connectable may be used without any problems while selecting a proper shape.

INDUSTRIAL APPLICABILITY

According to the container for processing section samples, the processing method for section samples, and the processing apparatus for section samples, a series of tapes carrying thereon thin section samples of biomedical tissues can be favorably positioned in case of observing the thin section samples without cutting the tape; moreover, the thin section samples of the biomedical tissue being carried on the tape can each be processed with different chemicals depending on the. Furthermore, thin section samples having processed corresponding to the variation in observations for the various types of biomedical tissues can be obtained.

The invention claimed is:

1. A processing method for section samples, comprising:
   a step of providing plural thin section samples on one side of an adhesive carrier tape by adhering the edge portion of a sample block obtained by embedding a specimen in an embedding material, and for predetermined times, carrying out the process of cutting out the vicinity of the edge portion of the sample block being adhered to the carrier tape in such a manner that the thin section samples are left on the carrier tape;
   a step for deforming the carrier tape by tightly adhering portions of the carrier tape disposed at a predetermined distance from each other along the longitudinal direction, in such a manner that the carrier tape itself constitutes the side wall and the bottom part, and that one of the thin section samples may be interposed inside the adhered portions;
   a step for injecting into the container a processing solution for processing thin section samples, and removing the processing solution from the container after a predetermined duration of time; and
   a step of releasing the tightly adhered portions of the carrier tapes.

2. A processing method for section samples as claimed in claim 1, wherein, the tightly adhered portions of the carrier tapes are fixed and supported by using a fixing unit after establishing the tight adhesion.

3. A processing apparatus for section samples, comprising:
   an adhesion unit which adheres on one side of an adhesive carrier tape, the edge portion of a sample block obtained by embedding a specimen in an embedding material;
   a cutting out unit which cuts out the vicinity of the edge portion of the sample block adhered to the carrier tape, in such a manner that the thin section samples are left over on the carrier tape;
   a carrier tape deformation unit for deforming the carrier tape by tightly adhering portions of the carrier tape disposed at a predetermined distance from each other along the longitudinal direction, in such a manner that the carrier tape itself constitutes the side wall and the bottom part, and that one of the thin section samples may be interposed inside the adhered portions;
   a processing solution injection unit for injecting a processing solution for processing the thin section samples into a container made of the side wall member and the bottom member;
   a processing solution removal unit for removing the processing solution from the container after passage of a predetermined time; and
   a release unit for releasing the mutual engaging and supporting of the side wall member and the bottom member that is established by the engaging unit.

* * * * *